(12) United States Patent
Krejci

(10) Patent No.: US 11,918,637 B2
(45) Date of Patent: Mar. 5, 2024

(54) VACCINATION AGAINST PORCINE CIRCOVIRUSES

(71) Applicant: Ceva Sante Animale, Libourne (FR)

(72) Inventor: Roman Krejci, Libourne (FR)

( * ) Notice: Subject to any disclaimer, the term of this patent is extended or adjusted under 35 U.S.C. 154(b) by 295 days.

(21) Appl. No.: 16/973,731

(22) PCT Filed: Jun. 10, 2019

(86) PCT No.: PCT/EP2019/065081
§ 371 (c)(1),
(2) Date: Dec. 9, 2020

(87) PCT Pub. No.: WO2019/238611
PCT Pub. Date: Dec. 19, 2019

(65) Prior Publication Data
US 2021/0338792 A1  Nov. 4, 2021

(30) Foreign Application Priority Data
Jun. 11, 2018 (EP) ...................... 18305709

(51) Int. Cl.
*A61K 39/12* (2006.01)
*A61P 31/20* (2006.01)
*A61K 39/00* (2006.01)

(52) U.S. Cl.
CPC .............. *A61K 39/12* (2013.01); *A61P 31/20* (2018.01); *A61K 2039/54* (2013.01); *A61K 2039/545* (2013.01); *A61K 2039/552* (2013.01)

(58) Field of Classification Search
None
See application file for complete search history.

(56) References Cited

U.S. PATENT DOCUMENTS

| | | | |
|---|---|---|---|
| 2010/0310589 A1* | 12/2010 | Kumar | A61P 31/00 119/665 |
| 2012/0164170 A1* | 6/2012 | Kuo | C07K 14/005 435/235.1 |
| 2014/0348874 A1* | 11/2014 | Segales | A61K 38/162 424/204.1 |

FOREIGN PATENT DOCUMENTS

| | | |
|---|---|---|
| JP | 2003502303 A | 1/2003 |
| JP | 2010513315 A | 4/2010 |
| JP | 2016531854 A | 10/2016 |
| WO | 20000077188 A | 12/2000 |
| WO | 20080076915 A | 6/2008 |
| WO | 20150048115 A | 4/2015 |

OTHER PUBLICATIONS

Martelli P, et al. Impact of maternally derived immunity on piglets' immune response and protection against porcine circovirus type 2 (PCV2) after vaccination against PCV2 at different age. BMC Vet Res. May 11, 2016;12:77. doi: 10.1186/s12917-016-0700-1. PMID : 27170186; PMCID: PMC4864921.*
Yeonsu Oh, Hwi Won Seo, Changhoon Park, Chanhee Chae. Comparison of sow and/or piglet vaccination of 3 commercial porcine circovirus type 2 (PCV2) single-dose vaccines on pigs under experimental PCV2 challenge. Veterinary Microbiology. vol. 172, Issues 3-4, 2014. pp. 371-380. ISSN 0378-1135.*
European Medicines Agency, Science Medicines Health. Circovac . EPAR summary for the public. EMA/286116/2007. EMEA/v/C/000114. European Commission Granted 2007. Last published May 2017.*
Rodibaugh, M. Vaccination Timing in Small Pigs and Sows. Boehringer Ingelheim. https://www.bivetmedica.com/species/swine/industry_support/show_pig/learn/vaccination_timinginsmallpigsandsows.html. Available on May 24, 2016 by WayBack Machine.*
Oliver Ferrando, S. Effect of Porcine circovirus (PCV2) sow or piglet vaccination in different PCV2 subclinical infection scenarios. PhD Thesis. Balterra, 2017. Universitat Autonoma de Barcelona, pp. 1-176.*
Office Action for corresponding JP Application No. 2020-568520 dated Mar. 23, 2023.
O'Neill, K. C., Hemann, M., Gimenez-Lirola, L. G., Halbur, P. G., & Opriessnig, T. (2012). Vaccination of sows reduces the prevalence of PCV-2 viraemia in their piglets under field conditions. Veterinary Record, 171(17), 425-425. doi:10.1136/vr.100660.

* cited by examiner

*Primary Examiner* — Benjamin P Blumel
*Assistant Examiner* — Jeffrey Mark Sifford
(74) *Attorney, Agent, or Firm* — SALIWANCHIK, LLOYD & EISENSCHENK

(57) ABSTRACT

The invention relates to compositions and methods for treating or preventing diseases caused by Porcine circoviruses. The invention particularly discloses methods for controlling PCV infection or disease in a pig herd, comprising (i) vaccinating sows against PCV at weaning, and (ii) vaccinating piglets against PCV at an age of between 2 to 7 weeks.

9 Claims, 2 Drawing Sheets

VACCINATION AGAINST PORCINE CIRCOVIRUSES

CROSS-REFERENCE TO RELATED APPLICATIONS

This application is a U.S. National Phase of PCT/EP2019/065081, filed Jun. 10, 2019, which claims priority of EPO patent application 18305709.0 filed Jun. 11, 2018, the contents thereof have been incorporated in their entirety.

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION BY REFERENCE OF A MATERIAL SUBMITTED ON A READ-ONLY OPTICAL DISK, AS A TEXT FILE OR AN XML FILE VIA THE PATENT ELECTRONIC SYSTEM

Not Applicable

STATEMENT REGARDING PRIOR DISCLOSURES BY THE INVENTOR OR A JOINT INVENTOR

Not Applicable

BACKGROUND OF THE INVENTION

Field of the Invention

The invention relates to compositions and methods for treating or preventing diseases caused by Porcine circoviruses.

Description of Related Art

Porcine circoviruses are a major class of viruses infecting pigs. Several types of PCV have been reported, including PCV1, PCV2 and PCV3. These viruses are present worldwide and have been infecting a vast majority of pig herds, especially PCV2. Some are non-pathogenic, but other can cause diseases (PCVD), including PCV2a, PCV2b, PCV2d, suspectedly also PCV3. PCV associated diseases include inter alia Postweaning Multisystemic Wasting Syndrome (PMWS), Porcine Dermatitis and Nephropathy Syndrome (PDNS), Porcine Respiratory Disease Complex (PRDC), reproductive disorders, granulomatous enteris, exudative epidermitis, necrotizing lymphadenitis, and congenital tremors.

The control of PCV infection and associated diseases (PCVD) in pig herds is therefore a major stake for breeders. It is today based mainly on vaccination. At present, different PCV vaccines are available for use in piglets, in particular anti-PCV2 vaccines. Such vaccines are either inactivated (e.g., killed) vaccines, or sub-unit vaccines. PCV vaccines, such as PCV2 vaccines, are able to reduce the viral burden and to control PCVD, such as by reducing viral-induced lesions in the lymphoid tissue. Depending on the conditions and status of vaccinated pigs, these vaccines can thus be fully effective. However, it was reported in piglets that maternally derived immunity can interfere negatively with the efficacy of such vaccines. In particular, it was mentioned that such interference may be related to the age of piglets at vaccination, to the timing of vaccination, and to the level of maternally derived immunity, for instance. Studies showed that high levels of maternally derived antibodies interfered with the humoral immune response after vaccination against PCV2 in piglets [22]. In piglets having a high level of passive immunity, a decline of antibody was observed upon vaccination. In addition, Haake et al suggested that vaccination at one week of age could alter the induction of an active humoral immunity in piglets.

The exact cause of MDA interference is still subject of investigations, but there is a need for optimized anti-PCV vaccination strategies or regimens which can provide strong protection in pig herds.

BRIEF SUMMARY OF THE INVENTION

The present application provides such novel methods for vaccinating pigs against PCV, and for controlling PCV infection or disease in pig herds.

More particularly, the invention relates to a method for controlling PCV infection or disease in a pig herd, comprising (i) vaccinating sows against PCV at weaning and (ii) vaccinating their piglets against PCV at an age of between 2 to 7 weeks.

According to the method of the invention, it has to be understood that sows are vaccinated against PCV at weaning of their piglets.

The inventors investigated the clinical protection (vaccine efficacy) conferred by such novel vaccination regimen and found that it can provide adequate protection, with a unique dose of vaccine, without the need to assess passively acquired immunity derived from gilts and sows. The combination of vaccination in sows at weaning and in their piglets at 2-7 weeks of age is highly effective for controlling PCV infection and associated diseases in pig herds, and does not appear to be subject to interference by maternally-derived immunity.

The invention more particularly relates to a method for controlling PCV infection or disease in pigs, comprising vaccinating sows and their piglets against PCV, wherein (i) sows are vaccinated against PCV at weaning and (ii) the piglets are vaccinated against PCV at an age of between 2 to 7 weeks.

The invention also relates to a method for vaccinating pigs against PCV infection or disease, comprising vaccinating sows and their piglets, wherein (i) sows are vaccinated against PCV at weaning and (ii) the piglets are vaccinated against PCV at an age of between 2 to 7 weeks.

The invention also particularly relates to a method for inducing protective anti-PCV immunity in pigs, comprising vaccinating sows and their piglets against PCV, wherein (i) sows are vaccinated against PCV at weaning and (ii) the piglets are vaccinated against PCV at an age of between 2 to 7 weeks.

The invention also relates to a method for controlling PCV infection or disease in a pig herd, comprising (i) vaccinating sows against PCV at weaning, and (ii) vaccinating piglets against PCV at an age of between 2 to 7 weeks; preferably the method comprises vaccinating sows and their piglets against PCV, wherein (i) sows are vaccinated against PCV at weaning and (ii) the piglets are vaccinated against PCV at an age of between 3 to 6 weeks.

The invention also relates to a PCV vaccine for use in a method for controlling PCV infection or disease in a pig herd, the method comprising (i) vaccinating sows against PCV at weaning, and (ii) vaccinating piglets against PCV at an age of between 2 to 7 weeks. Preferably, the method comprises vaccinating sows and their piglets against PCV, wherein (i) sows are vaccinated against PCV at weaning and (ii) the piglets are vaccinated against PCV at an age of between 3 to 6 weeks.

The invention also relates to a PCV vaccine for use for vaccinating pigs against PCV infection or disease, comprising vaccinating sows and their piglets, wherein (i) sows are vaccinated against PCV at weaning and (ii) the piglets are vaccinated against PCV at an age of between 2 to 7 weeks.

The invention also relates to a PCV vaccine for use for inducing protective anti-PCV immunity in pigs, comprising vaccinating sows and their piglets against PCV, wherein (i) sows are vaccinated against PCV at weaning and (ii) the piglets are vaccinated against PCV at an age of between 2 to 7 weeks.

The invention also relates to the use of a PCV antigen for the manufacture of a vaccine for controlling PCV infection or disease in a pig herd by (i) vaccinating sows against PCV at weaning, and (ii) vaccinating piglets against PCV at an age of between 2 to 7 weeks. Preferably, the use comprises vaccinating sows and their piglets against PCV, wherein (i) sows are vaccinated against PCV at weaning and (ii) the piglets are vaccinated against PCV at an age of between 3 to 6 weeks.

The invention also relates to the use of a PCV antigen for the manufacture of a composition for vaccinating pigs against PCV infection or disease by vaccinating sows and their piglets, wherein (i) sows are vaccinated against PCV at weaning and (ii) the piglets are vaccinated against PCV at an age of between 2 to 7 weeks.

The invention also relates to the use of a PCV antigen for the manufacture of a PCV vaccine for inducing protective anti-PCV immunity in pigs by vaccinating sows and their piglets against PCV, wherein (i) sows are vaccinated against PCV at weaning and (ii) the piglets are vaccinated against PCV at an age of between 2 to 7 weeks.

The inventors have found that when sow are vaccinated at weaning (i.e., at weaning of their piglets), the next generation piglets will be highly responsive to vaccination at the age of 2-7 weeks. As a result, piglets can be effectively protected by a single vaccination, and sow may be vaccinated at each weaning.

In a most preferred embodiment, the piglets are vaccinated at 3 weeks of age or at 6 weeks of age.

In a typical embodiment, the sows and their piglets are vaccinated at weaning, i.e., essentially on the same day.

In a specific and advantageous embodiment, vaccination of the sows and piglets comprises a single injection of a PCV vaccine, such as a single intramuscular injection of a PCV vaccine.

The invention may be used with any PCV vaccine, and is particularly suited to vaccinate against PCV2, even more particularly using inactivated PCV2 vaccines.

DETAILED DESCRIPTION OF THE INVENTION

Vaccine Compositions

Figure 1:
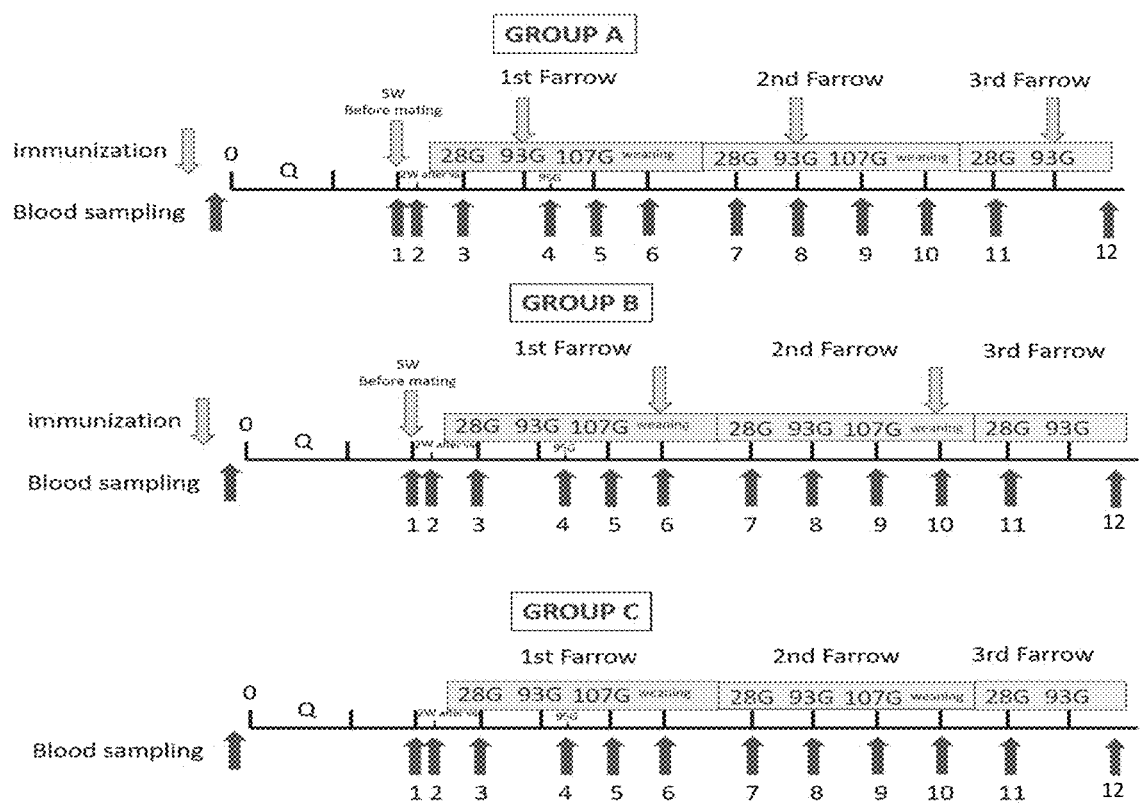
FIG. 1 illustrates an immunization protocol of clinical study B.

The term "vaccine" as used herein includes any composition which may be used to cause, stimulate or amplify an immune response in an animal (e.g., pigs) against a PCV.

The vaccines thus comprise at least one antigen from the target virus. The antigen may be, without limitation, the whole virus (in inactivated or attenuated form), an extract or fraction thereof, an isolated viral protein or other viral component, a nucleic acid encoding the same, or fragments or derivatives thereof.

Vaccines may comprise, in addition to the antigen (or immunogen), other ingredients, known per se by one of ordinary skill in the art, such as pharmaceutically acceptable carriers, excipients, diluents, adjuvants, freeze drying stabilizers, wetting or emulsifying agents, pH buffering agents, gelling or viscosity enhancing additives, or preservatives, depending on the route of administration.

Examples of pharmaceutically acceptable carriers, excipients or diluents include, but are not limited to demineralised or distilled water; saline solution; vegetable based oils such as peanut oil, arachis oil, safflower oil, olive oil, cottonseed oil, maize oil, sesame oil, or coconut oil; silicone oils, including polysiloxanes, such as methyl polysiloxane, phenyl polysiloxane and methylphenyl polysolpoxane; volatile silicones; mineral oils such as light liquid paraffin oil, or heavy liquid paraffin oil; squalene; cellulose derivatives such as methyl cellulose, ethyl cellulose, carboxymethylcellulose, carboxymethylcellulose sodium salt, or hydroxypropyl methylcellulose; lower alkanols, for example ethanol or iso-propanol; lower aralkanols; lower polyalkylene glycols or lower alkylene glycols, for example polyethylene glycol, polypropylene glycol, ethylene glycol, propylene glycol, 1,3-butylene glycol or glycerin; fatty acid esters such as isopropyl palmitate, isopropyl myristate or ethyl oleate; polyvinylpyrrolidone; agar; carrageenan; gum tragacanth or gum acacia, and petroleum jelly. Typically, the carrier or carriers will form from 10% to 99.9% by weight of the vaccine composition and may be buffered by conventional methods using reagents known in the art, such as sodium hydrogen phosphate, sodium dihydrogen phosphate, potassium hydrogen phosphate, potassium dihydrogen phosphate, a mixture thereof, and the like.

Examples of adjuvants include, but are not limited to, oil in water emulsions, aluminum hydroxide (alum), immunostimulating complexes, non-ionic block polymers or copolymers, cytokines (like IL-1, IL-2, IL-7, IFN-[alpha], IFN-[beta], IFN-y, etc.), saponins, monophosphoryl lipid A (MLA), muramyl dipeptides (MDP) and the like. Other suitable adjuvants include, for example, aluminum potassium sulfate, heat-labile or heat-stable enterotoxin(s) isolated from *Escherichia coli*, cholera toxin or the B subunit thereof, diphtheria toxin, tetanus toxin, pertussis toxin, Freund's incomplete or complete adjuvant, etc. Toxin-based adjuvants, such as diphtheria toxin, tetanus toxin and pertussis toxin may be inactivated prior to use, for example, by treatment with formaldehyde.

Examples of freeze-drying stabilizer may be for example carbohydrates such as sorbitol, mannitol, starch, sucrose, dextran or glucose, proteins such as albumin or casein, and derivatives thereof.

Vaccines may also comprise antigens from other pathogens, such as *Actinobacillus pleuropneumoniae*; Adenovirus; Alphavirus such as Eastern equine encephalomyelitis viruses; *Balantidium coli; Bordetella bronchiseptica; Brachyspira* spp., preferably *B. hyodyentheriae, B. pilosicoli, B. innocens, Brucella suis*, preferably biovars 1, 2 and 3; Classical swine fever virus, African swine fever virus; *Chlamydia* and *Chlamydophila* sp. and preferably *C. pecorum* and *C. abortus; Clostridium* spp., preferably *Cl. difficile, Cl. perfringens* types A, B and C, *Cl. novyi, Cl. septicum, Cl. tetani*; Digestive and respiratory Coronavirus; *Cryptosporidium parvum; Eimeria* spp; *Eperythrozoonis suis* currently named *Mycoplasma haemosuis; Erysipelothrix rhusiopathiae; Escherichia coli; Haemophilus parasuis*, preferably subtypes 1, 7 and 14; Hemagglutinating encephalomyelitis virus; *Isospora suis*; Japanese Encephalitis virus; *Lawsonia intracellular; Leptospira* spp., preferably *Leptospira australis, Leptospira canicola, Leptospira grippotyphosa, Leptospira icterohaemorrhagicae, Leptospira interrogans, Leptospira Pomona* and *Leptospira tarassovi; Mannheimia haemolytica; Mycobacterium* spp. preferably, *M. avium, M. intracellular* and *M. bovis; Mycoplasma hyponeumoniae*; Parvovirus; *Pasteurella multocida; Porcine cytomegolovirus; Porcine parovirus*; Porcine reproductive and respiratory syndrome virus; Pseudorabies virus; Rotavirus; Sagiyama virus; *Salmonella* spp. preferably, *S. typhimurium* and *S. choleraesuis; Staphylococcus* spp. preferably, *S. hyicus; Streptococcus* spp., preferably Strep, suis; Swine cytomegalovirus; Swine herpes virus; Swine influenza virus; Swinepox virus; *Toxoplasma gondii*; Vesicular stomatitis virus and/or virus of exanthema of swine.

The vaccine compositions of the invention may be liquid formulations such as an aqueous solution, water-in-oil or oil-in-water emulsion, syrup, an elixir, a tincture, a preparation for parenteral, subcutaneous, intradermal, intramuscular or intravenous administration (e.g., injectable administration), such as sterile suspensions or emulsions. Such formulations are known in the art and are typically prepared by dissolution of the antigen and other typical additives in the appropriate carrier or solvent systems. Liquid formulations also may include suspensions and emulsions that contain suspending or emulsifying agents.

Administration Regimen

The invention provides an improved PCV vaccination regimen in pigs which comprises essentially one administration in sows at weaning and one administration in piglets at 3-6 weeks of age. In a typical embodiment, the sows and their piglets are essentially treated on the same day, at weaning. Such vaccination effectively protects the piglets without the need to assess MDA. Such vaccination regimen effectively protects the sow until the next weaning. Such vaccination ensures effective vaccination of next generation piglets by a single vaccination at 3-6 weeks of age.

The route of administration can be percutaneous, via mucosal administration, or via other parenteral routes (intradermal, intramuscular, subcutaneous, intravenous, or intraperitoneal). The vaccine of the invention can conveniently be administered intranasally, transdermally (i.e., applied on or at the skin surface for systemic absorption), parenterally, ocularly, etc. The parenteral route of administration includes, but is not limited to, intramuscular, intravenous, intraperitoneal routes and the like. Intramuscular is preferred.

The vaccines of the invention can be administered as single doses. Furthermore, the vaccines of the invention can be administered alone, or can be administered simultaneously or sequentially administered with one or more further compositions, such as for example other porcine immunogenic or vaccine compositions.

In practice, the exact amount required for an immunologically effective dose may vary from subject to subject depending on factors such as the age and general condition of the subject, the nature of the formulation and the mode of administration. Appropriate "effective amount" may be determined by one of ordinary skill in the art using only routine experimentation. For instance, methods are known in the art for determining or titrating suitable dosages of a vaccine to find minimal effective dosages based on the weight of the non-human animal subject, concentration of the vaccine and other typical factors. In a typical embodiment, the vaccine comprises a unitary dose of between 0.5-5 ml. Most preferably, sows are administered between 2-4 ml and piglets are administered between 0.5-3 ml.

In a particular embodiment, the invention relates to a method of controlling PCV infection or disease in herds. Controlling PCV infection or disease designates, inter alia, preventing, or reducing, or limiting PCV infection and associated diseases, preventing or reducing or limiting PCV spread in a herd; preventing or reducing or limiting occurrence or severity of a PCV-associated disease; or reducing PCV viral load.

PCV2 Vaccination

In a preferred embodiment, the invention is used to vaccinate pigs against PCV2 or to control PCV2 infection or disease. The invention thus uses a PCV2 vaccine.

Currently developed PCV2 vaccines, such as Circovac® (Ceva), Ingelvac®, CircoFLEX® (recombinant vaccine porcine circovirus type 2, PCV 2) (Boehringer Ingelheim Vetmedica), or Suvaxyn®, are either inactivated PCV2 vaccines or Sub-Unit vaccines. PCV2 Sub-Unit vaccines typically use a purified, recombinant PCV2a capsid protein produced by recombinant expression of the ORF2 gene of PCV2a. In this regard, the protein encoded by ORF2 of PCV2 isolates Imp 1011 has been reported in EP1741785. A protein encoded by ORF2 of PCV2 isolate PCV2Rm has been reported in WO2010/061000. The protein encoded by ORF2 of PCV2 isolate 412 has been reported in EPI 816200. Another protein encoded by an ORF2 of a further PCV2 isolate has been reported in EP 1036180 or EP2225367. Improved synthetic ORF2-type proteins have been described in WO2013/030320 and in WO2014/167060.

In a particular embodiment, the present invention uses a PCV2 vaccine which is an inactivated PCV2 vaccine. The vaccine may comprise any inactivated PCV2 strain, such as an inactivated PCV2a, an inactivated PCV2b or an inactivated PCV2d. A specific example is Circovac®.

In another particular embodiment, the invention uses a PCV2 vaccine which is a sub-unit vaccine containing (or expressing) a PCV2 ORF2 polypeptide or a fragment thereof. In a particular embodiment, the ORF2 is selected from ORF2 of PCV2 isolates Imp1011, PCV2Rm, or 412, or a ORF2 having at least 80% sequence identity to such proteins, or an immunogenic fragment thereof comprising at least 10, 15, more preferably at least 20 contiguous amino acid residues thereof.

Further aspects and advantages of the invention shall be disclosed in the following experimental section, which illustrates the claimed invention.

Examples

Clinical Study A
Study Design

The study is performed at one Italian pig farm with a confirmed diagnosis of PCVD, according to the criteria of the EU consortium on PCVD research. The study is carried out according to a randomised, controlled and blinded design.

Sows pre-enrolment: 150 sows are bled at mid gestation for the detection of ELISA antibodies to PCV2 and the calculation of the S/P value. Three groups of 50 sows each are organised and allocated to three different groups equalized according to: a) the average parity of the; b) the mean S/P value.

Sows enrolment: Three groups of 50 sows are treated as follows:
  group A: vaccinated at weaning (V1);
  group B: vaccinated five and three weeks before the expected date of farrowing only (V2);
  group C: non-vaccinated/Control (NV)

One week before the expected farrowing date all sows are bled.

Piglets enrolment: Approximately 900 suckling piglets ageing three weeks of age (not less than 100 piglets per study group) are admitted to the study.

At admission to the study the piglets from the over mentioned sows (groups A, B and C) are individually identified by ear tagging, 40% of the animals are weighted and 20% are bled at each time sampling.

The piglets are then randomly allocated to one of the three study groups within the individual litters. All piglets receive intra-muscular injection of Circovac® (left side), one group (A) at 3 weeks of age, and the other group (B) at 6 (six) weeks of age. One group (C) is injected with saline (placebo) and kept as negative control.

|  | Piglets vaccination | | |
| --- | --- | --- | --- |
| Sow vaccination | 3 weeks of age (A) | 6 weeks of age (B) | Non-vaccinated/Control (C) |
| At weaning (40) (V1) | 100 (V1-A) | 100 (V1-B) | 100 (20*) (V1-C) |
| 5 + 3 weeks before farrowing (40) (V2) | 100 (V2-A) | 100 (V2-B) | 100 (20*) (V2-C) |
| Control - non vaccinated (40) (NV) | 100 (NV-A) | 100 (NV-B) | 100 (20*) (NV-C) |

*to be weighted at different time points

The body weight of the piglets is measured at admission, at the end of the nursery phase and at 6 month of age. Carcasses weight at slaughter are recorded if possible. The individual treatments, which are administered to the piglets, are recorded as a measure of the morbidity. Post-mortem examination is performed on each dead piglet to determine the cause of death, except in cases where the cause of death is clear and non-PCV2 related (e.g. piglets crushed by the sow, broken leg etc.).

Average daily weight gain, morbidity and mortality and PCV2 viremia are compared between the study groups as primary parameters of the vaccination scheme efficacy.

Blood samples are taken from 20 piglets per group according to the timing exhibited in table 1.

Weighing time is also shown in table 1.

All piglets are monitored for vaccination reactions immediately after vaccination and at 1 day, at 1 week and then weekly until all reactions have disappeared.

TABLE 1

Timing for sampling and weighing

| Sows | | | |
| --- | --- | --- | --- |
| Time of sampling | V1 | V2 | NV |
| Pre-enrolment Middle of previous gestation | 150 sows blood sampling | | |
| One week pre-farrowing | 150 sows blood sampling | | |

| Piglets | | | |
| --- | --- | --- | --- |
| Week of age | Group A | Group B | Group C |
| 3 | Enrolment and Weighing | | |
| 3 | Blood sampling Vaccination | | Blood sampling |
| 6 | Blood sampling | Blood sampling Vaccination | Blood sampling |
| 9 | Blood sampling | Blood sampling | Blood sampling |
| 12 | Blood sampling | Blood sampling Weighing | Blood sampling |
| 15 | Blood sampling | Blood sampling | Blood sampling |
| 18 | Blood sampling | Blood sampling | Blood sampling |
| 21 | Blood sampling | Blood sampling | Blood sampling |
| 24 | Blood sampling | Blood sampling | Blood sampling |
| 27 | Blood sampling | Blood sampling Weighing | Blood sampling |
| 30 | Blood sampling | Blood sampling | Blood sampling |
| 33 | Blood sampling | Blood sampling | Blood sampling |
| 36 | Blood sampling | Blood sampling | Blood sampling |

Test Product
Investigational Article
Product: Circovac® (CEVA)
Composition/Titre: INACTIVATED PCV2 vaccine
Presentation: 100 ml PET vials
Animals Nine hundreds of healthy piglets (100 for each group) of approximately three weeks of age are included in the study. All piglets come from sow vaccinated as young piglets and boosted at first breeding. The sows are vaccinated at weaning of the previous lactation or 5 and 3 weeks before farrowing (2 GROUPS OF SOWS) according to the scheme exhibited at point 2.

Husbandry
The study animals (all groups mixed) are housed as standard on the farm.
The study animals are fed as standard on the farm.
Blinding
The study is blinded. The vials of the vaccines will only be identified by the label code.
Treatment
  dose: 2 ml in sows and 0.5 ml in piglets
  route: By intramuscular injection
  Injection site: in the left side of the neck
    group A at 3 weeks of age
    group B at 6 weeks of age
    group C non-vaccinated
Assessment of Effects
The following parameters are used to assess the efficacy of the different vaccination protocols.
  i. Average daily weight gain (ADWG)
  ii. Mortality, including culled animals and causes of death
  iii. Morbidity (individual treatments/injection)
  iv. Proportion of PCR positive animals to PCV2
  v. Viral load (Q-PCR) of PCV2 from blood samples vi. Serological profiling for PRRSV and M hyo.
vii. Necropsy and microbiological investigations on spontaneously dead animals and humanely euthanised
viii. Lung lesions scoring at slaughterhouse The kinetics of the humoral and cell-mediated immune response is measured by ELISA serology (INGENASA) and by ELISpot for IFN-gamma SCs, respectively. These investigations take place on stored blood samples and PBMCs.

Moreover, the antibody titres to PCV2 are determined in order to assess the level of maternally derived antibody and the immune response to vaccination and the timing of field infection.

Viral load (Q-PCR) of PCV2 from blood samples According to standard procedures Q-PCR for PCV2.

Serology

Serological response to vaccination and infection is measured by using commercially available kits [IDEXX laboratories (PRRS and Mhyo) and INGENASA (PCV2) IgM+ IgG]

After clotting, the serum is divided in 2 serum tubes and the samples are stored at ≤−18° C. until analysis.

Cell-Mediated Immune Response

The cell mediated immune response is measured by ELISpot assay to determine IFN-gamma SCs.

IFN-γ ELISpot assay. Peripheral Blood Mononuclear Cells (PBMC) are isolated by density gradient in Histopague-1077® solution by a centrifugation step at 420×g (1800 rpm) for 30'.

At the end PBMC are recovered by aspiration and resuspended in RPMI-1640 medium to be plated at the density of 200.000 cells/200 μl RPMI-1640 supplemented with 10% FCS in 96-well plates coated with anti-IFN-γ monoclonal antibody (P2G10—BD Pharmingen). Antigen stimulation in vitro is performed by PCV2 antigen (virus: 0.1-1 MOI; order of magnitude: μg/ml) for at least 20 hours.

IFN-γ secretion by PBMC is detected by using an anti-IFN-γ (P2C11—BD Pharmingen) biotin-conjugated monoclonal antibody, a secondary alkaline phosphatase-conjugated antibody (Vector) and an NBT/BCIP developing substrate solution (BioRad). The reaction is visualised as blue spots due to precipitation of the substrate where cells secreted IFN-γ by an AID® ELISpot Reader.

Lung Lesions at Slaughterhouse

At slaughterhouse lung lesions are checked according to the Madec's gride and SPES grid.

The results of these experiments allow to confirm the clinical protection (vaccine efficacy) conferred by such novel vaccination regimen and that it can provide adequate protection, with a unique dose of vaccine, without the need to assess passively acquired immunity derived from gilts and sows.

Clinical Study B

| Vaccination Cricovac | Group A | Group B | Group C |
|---|---|---|---|
| After quarantine 1 time | + | + | − |
| 3 W before first farrowing | + | − | − |
| At Weaning | − | + | − |
| 3 W before 2nd farrowing | + | − | − |
| At Weaning | − | + | − |
| 3 W before 3rd farrowing | | | |

To assess viremia and immune responses, 12 blood samples were taken to each animal throughout the study at the dates indicated by arrows on FIG. 1. The mean value of anti-PCV2 IgG in sows and in the piglets are presented FIG. 2 and FIG. 3.

Figure 2:
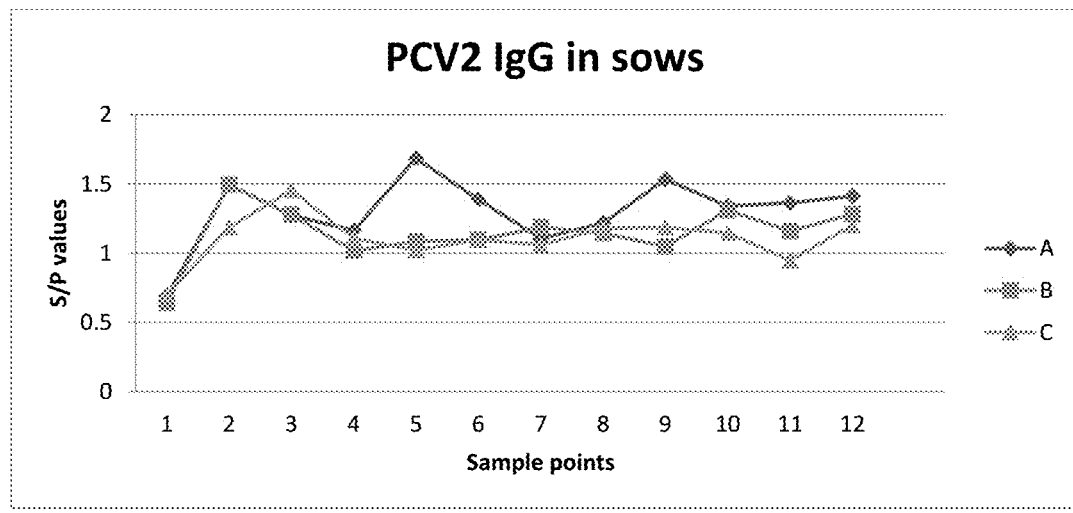
FIG. 2 shows the PCV2 IgG levels in sows.

The results of FIG. 2 clearly show that the vaccination induced production of specific antibodies in sows. It is striking that in sows of group B the titers were more homogenous than in group A. Group A sows had always high titers before each farrowing as a response to the pre-farrow booster vaccinations. We do not see those peaks in sows of group B. That means group B sows did not have so high concentrations of antibodies shortly before farrowing to be transferred into colostrum and consequently appearing in the blood of piglets as MDAs.

Figure 3:
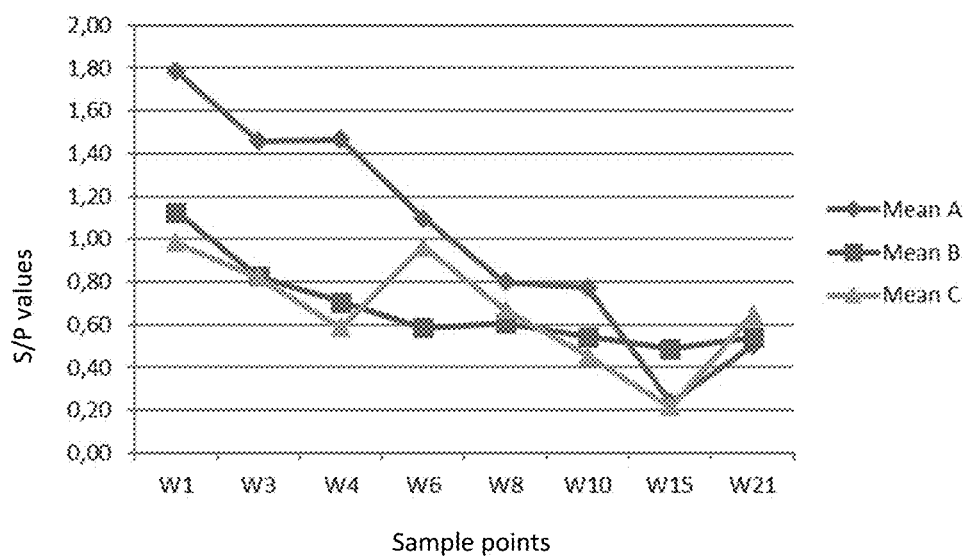
FIG. 3 shows the PCV2 IgG levels in piglets.

Similarly, it can be seen from FIG. 3 that piglets born to sows of group A show much higher titers of antibodies week 1 and also week 3 of life. Furthermore, a very high variation of the titers is observed within group A. In contrast, piglets born to first parity sows B (first farrowing) have moderate titers week 1 and relatively low titers week 3, and piglets born to second parity sows of group B (second farrowing) have very high titers week 1 (which does not interfere since we do not vaccinate at this age) and moderate titers week 3, at the time of vaccination. Also, the titers week 3 are much more homogenous than in piglets of group A and also of group C (control, non-vaccinated sows). Some of piglets of group C have also high titers, probably because their mothers were infected and produced postinfectious antibodies. Their titers are much more variable than in piglets of the group B.

The immunization profile of group B is thus advantageous since we wanted to achieve homogenous level of immune status in sows to protect themselves and also an appropriate (not too high), homogenous immune status (level of MDAs) in piglets to protect them without causing interference with the vaccination.

The results of these experiments thus further confirm the clinical protection (vaccine efficacy) conferred by such novel vaccination regimen and that it can provide adequate protection, with a unique dose of vaccine, without the need to assess passively acquired immunity derived from gilts and sows.

The invention claimed is:

1. A method for controlling Porcine circovirus of type 2 (PCV2) infection or disease in a pig herd, the method comprising vaccinating sows and their piglets against PCV2 with a PCV2 vaccine, wherein (i) sows are vaccinated at weaning of their piglets, and (ii) piglets are vaccinated at an age of between 2 to 7 weeks.

2. The method of claim 1, comprising vaccinating sows and their piglets against PCV2 infection or disease, wherein (i) sows are vaccinated against PCV2 infection or disease at weaning of their piglets and (ii) the piglets are vaccinated against PCV2 infection or disease at an age of between 3 to 6 weeks.

3. The method of claim 1, comprising vaccinating piglets at 3 weeks of age.

4. The method of claim 1, comprising vaccinating piglets at 6 weeks of age.

5. The method of claim 1, comprising vaccinating sows and their piglets at weaning on the same day.

6. The method of claim 1, wherein vaccination of the sows and piglets is performed with an inactivated PCV2 vaccine.

7. The method of claim 1, wherein vaccination of the piglets consists of a single injection of the PCV2 vaccine.

8. The method of claim 1, wherein vaccination of the piglets consists of a single intramuscular injection of the PCV2 vaccine.

9. The method of claim 1, wherein the sows are vaccinated at each weaning of their piglets.

* * * * *

UNITED STATES PATENT AND TRADEMARK OFFICE
CERTIFICATE OF CORRECTION

| | |
|---|---|
| PATENT NO. | : 11,918,637 B2 |
| APPLICATION NO. | : 16/973731 |
| DATED | : March 5, 2024 |
| INVENTOR(S) | : Roman Krejci |

It is certified that error appears in the above-identified patent and that said Letters Patent is hereby corrected as shown below:

In the Specification

Column 2,
Line 11, "Haake et al" should read --Haake et al [11]--.

Column 9,
Line 52,
"Clinical Study B" should read
--Clinical Study B
    Three groups of gilts, 10 animals each, were vaccinated with Circovac® (2 mL), following the vaccination regimen represented in the following Table:--.
Line 55, "Vaccination Cricovac" should read --Vaccination Circovac®--.

Signed and Sealed this
Twelfth Day of November, 2024

Katherine Kelly Vidal
*Director of the United States Patent and Trademark Office*